(12) United States Patent
Qanaei

(10) Patent No.: US 9,074,950 B2
(45) Date of Patent: Jul. 7, 2015

(54) PIPELINE INSPECTION GAUGE (PIG) ALERT SYSTEM

(71) Applicant: Ahmd Abdallah Al-Jassem Qanaei, Salwa (KW)

(72) Inventor: Ahmd Abdallah Al-Jassem Qanaei, Salwa (KW)

(*) Notice: Subject to any disclaimer, the term of this patent is extended or adjusted under 35 U.S.C. 154(b) by 440 days.

(21) Appl. No.: 13/654,131

(22) Filed: Oct. 17, 2012

(65) Prior Publication Data

US 2014/0102205 A1    Apr. 17, 2014

(51) Int. Cl.
*F16L 55/48* (2006.01)
*G01L 7/00* (2006.01)
*G01N 27/90* (2006.01)

(52) U.S. Cl.
CPC ............... *G01L 7/00* (2013.01); *G01N 27/902* (2013.01); *F16L 55/48* (2013.01)

(58) Field of Classification Search
None
See application file for complete search history.

(56) References Cited

U.S. PATENT DOCUMENTS

| | | | | |
|---|---|---|---|---|
| 3,553,672 | A * | 1/1971 | Smith | 340/627 |
| 4,389,880 | A * | 6/1983 | Robinet | 73/86 |
| 4,768,373 | A * | 9/1988 | Spencer | 73/86 |
| 4,899,903 | A | 2/1990 | Miyasaka et al. | |
| 5,211,677 | A * | 5/1993 | Sargeant et al. | 73/61.71 |
| 6,170,529 | B1 | 1/2001 | Howe | |
| 6,769,291 | B1 | 8/2004 | Julian et al. | |
| 7,854,337 | B1 | 12/2010 | Ismert et al. | |
| 2004/0212510 | A1 * | 10/2004 | Aronstam | 340/606 |
| 2005/0076724 | A1 * | 4/2005 | Boudreaux | 73/866.5 |
| 2012/0018177 | A1 * | 1/2012 | Eckholm et al. | 169/16 |

* cited by examiner

*Primary Examiner* — Robert R Raevis
(74) *Attorney, Agent, or Firm* — Richard C Litman

(57) ABSTRACT

The pipeline inspection gauge (PIG) alert system provides a method and apparatus for effectively locating a pipeline inspection gauge (PIG) as it traverses a pipeline. The method and apparatus incorporates hollow, empty tubes spaced along the length of the pipeline. The tubes are provided with lower ends that extend into the pipeline. The tubes are closed at their lower ends and connectable to respective pressure detection devices or the like at their upper ends. When a PIG passes through the pipeline, it contacts the lower end of the tube that extends into the pipeline, causing the tube to break, and thus opening the interior of the tube to the pressurized flow of the product flowing in the pipeline. The change in pressure is registered by the pressure detection device to indicate the passage of the PIG.

7 Claims, 3 Drawing Sheets

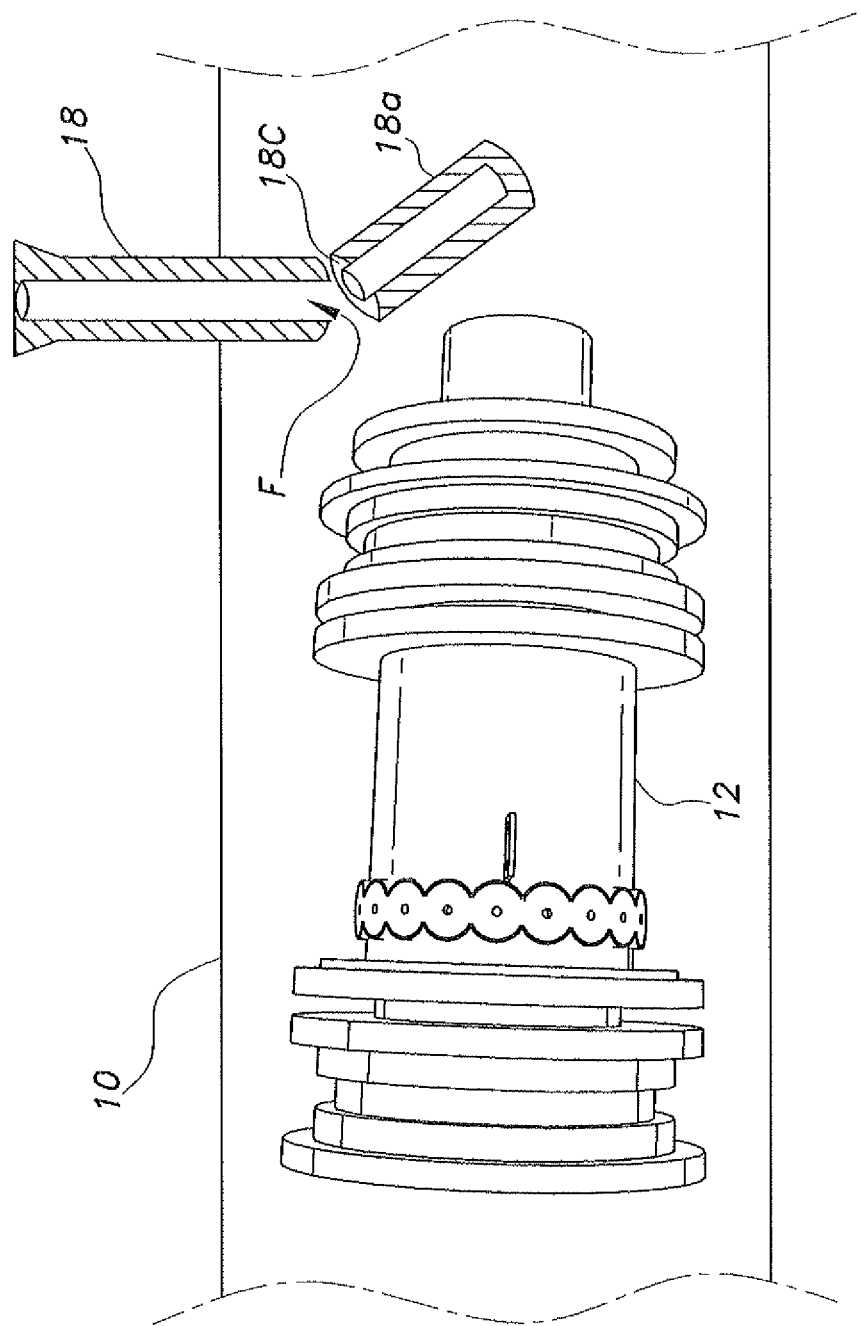

PIPELINE INSPECTION GAUGE (PIG) ALERT SYSTEM

BACKGROUND OF THE INVENTION

1. Field of the Invention

The present invention generally relates to pipeline inspection methods and apparatus therefor, and particularly to a pipeline inspection gauge (PIG) alert system for determining the presence and location of a pipeline inspection gauge (PIG) within a pipeline.

2. Description of the Related Art

The use of pipelines to convey liquid, semi-liquid, and gaseous products is commonplace in the industrial world. Pipelines are employed to convey products as diverse as crude oil, paints, liquid cosmetics, liquid foodstuffs, natural gas and the like. The integrity of the pipeline is vital to the conveying process. The disruption of flow caused by a ruptured or clogged pipeline can result in extensive monetary losses and may pose a danger to property and human life. Thus, the pipeline requires periodic inspection and cleaning to ensure that integrity is maintained.

In the context of pipelines, "pigging" refers to the practice of employing a pipeline inspection gauge (PIG) to perform the inspection and/or cleaning tasks necessary to maintain the integrity of the pipeline. The PIG can be fitted with scrapers and brushes to clean the inner walls of the pipeline and/or provided with electronic sensors to determine pipe thickness and corrosion areas along the pipeline. The PIG does not disrupt the product flow in the pipeline. The flow propels the PIG along the pipeline. Usually a PIG is inserted in the pipeline at a launching station and retrieved at a receiving station. There may be several launching and retrieving stations spaced along the length of a pipeline. It is important in the procedure to determine if the PIG has been successfully launched and when the PIG arrives at a receiving station. In oil and natural gas pipelines this determination has required the manipulation of heavy gates, which makes for a time-consuming and inefficient process procedure in locating the PIG. Alternatively, expensive and delicate electronic apparatus has been applied to determine the location of the PIG in the pipeline. The industry would certainly embrace an inexpensive and reliable procedure and apparatus for locating a PIG as it proceeds through the pipeline. Thus, a pipeline inspection gauge alert system solving the aforementioned problems is desired.

SUMMARY OF THE INVENTION

The pipeline inspection gauge (PIG) alert system provides a method and apparatus for effectively locating a pipeline inspection gauge as it traverses a pipeline. The method and apparatus incorporates hollow, empty tubes spaced along the length of the pipeline. The tubes are provided with lower ends that extend into the pipeline. The tubes are closed at their lower ends and connectable to respective pressure detection devices or the like at their upper ends. When a PIG passes through the pipeline, it contacts the lower end of the tube that extends into the pipeline, causing the tube to break, and thus opening the interior of the tube to the pressurized flow of the product flowing in the pipeline. The change in pressure is sensed by the pressure detection device to indicate the passage of the PIG. The tubes may be scored to facilitate a clean break.

Accordingly, the invention presents a system that provides means to detect the passage of a PIG in a pipeline. The system is reliable and efficient in operation. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

FIG. 3 is a diagrammatic section view of a pipeline inspection gauge (PIG) alert system according to the present invention, showing the PIG breaking a location tube in the pipeline.

Similar reference characters denote corresponding features consistently throughout the attached drawings.

DETAILED DESCRIPTION OF THE PREFERRED EMBODIMENTS

Figure 1:
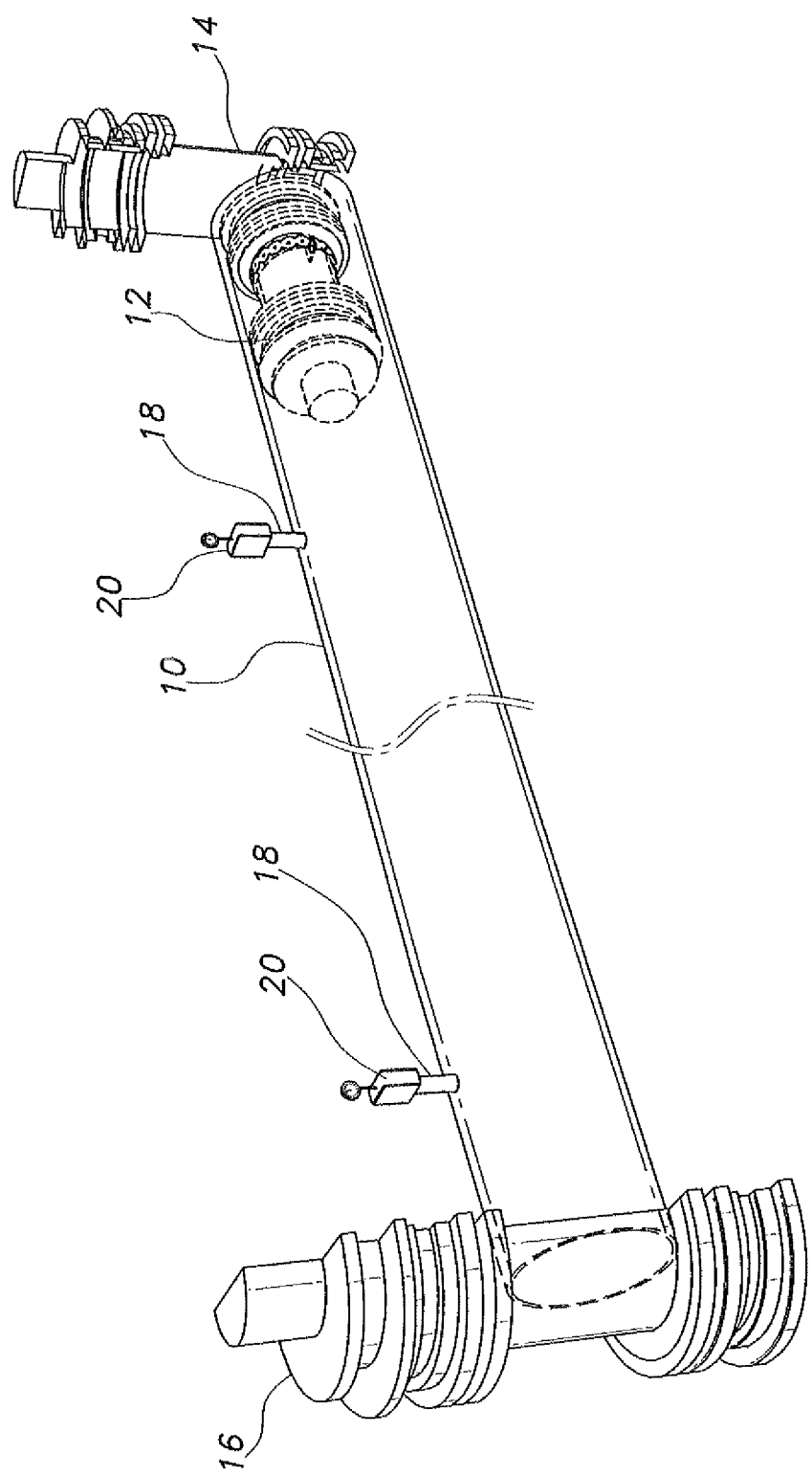
FIG. 1 is an environmental perspective view of a pipeline inspection gauge (PIG) alert system according to the present invention for determining the position of a PIG in a pipeline.
Figure 2:
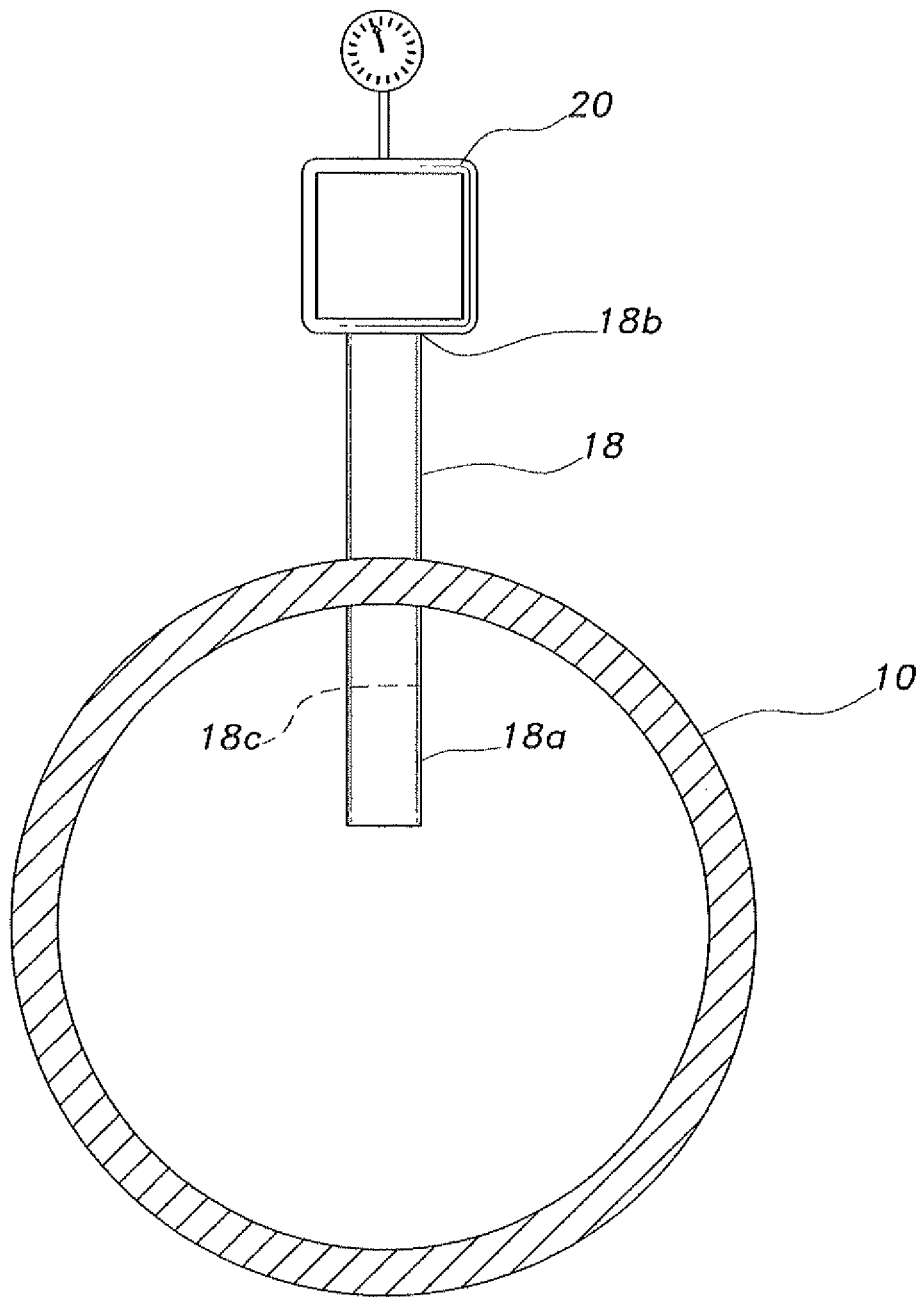
FIG. 2 is an end view in section of a pipeline inspection gauge (PIG) alert system according to the present invention.

Referring to FIGS. 1-3, a pipeline for transporting fluids is indicated at 10. A PIG 12 is positioned in the pipeline 10 for traversing the pipeline for purposes as discussed above. A launching station 14 is provided to insert the PIG 12 into the pipeline 10. A receiving station 16 is provided to retrieve the PIG 12 from the pipeline 10. The launching and receiving stations 14, 16 are conventional.

PIG location tubes 18 are positioned adjacent the launching and receiving stations 14, 16 to indicate when the PIG 12 has been successfully launched and when the PIG 12 has arrived at the receiving station 16 and is available for retrieval therefrom. The tubes 18 may be positioned at any desired position(s) along the pipeline 10, and are not limited to the above described locations. The tubes 18 are hollow and are closed at their lower end 18a. The upper end 18b of the tube communicates with a pressure detection device. A simple pressure gauge 20 is preferred. It should be noted however that other more sophisticated detection devices (transducers, flow switches, pressure switches, etc.) may be employed, if desired. The tubes 18 are preferably fabricated from plastic material. The circumference of the tube 18 may be scored at 18c (shown in phantom lines) near the lower end 18a for reasons indicated above. When the PIG 12 breaks the tube 18 (as shown diagrammatically in FIG. 3), the interior of the tube 18 is exposed to the flow pressure F of the product flowing in the pipeline 10. This pressure is detected by the pressure gauge 20, which indicates that the PIG 12 has arrived at that location.

It is to be understood that the present invention is not limited to the embodiments described above, but encompasses any and all embodiments within the scope of the following claims.

I claim:

1. A pipeline inspection gauge (PIG) alert system for detecting the location of a pipeline inspection gauge in a pipeline, the system comprising:

a plurality of tubes adapted for being positioned at spaced intervals along the length of the pipeline, each of the tubes having a lower end and an upper end, the lower end of each tube being adapted for extending into the pipeline, wherein each said tube has an exterior surface, the exterior surface being scored adjacent the lower end to facilitate breaking said tube adjacent the lower end; and means for detecting a change in pressure in each of the tubes, the means for detecting being disposed on the upper end of each of the tubes.

2. The pipeline inspection gauge (PIG) alert system according to claim 1, wherein the lower end of each said tube is closed and the upper end is open, said means for detecting being disposed in and sealing the upper end of said tube.

3. The pipeline inspection gauge (PIG) alert system according to claim 1, wherein each said tube is fabricated from plastic material.

4. The system for detecting the location of a pipeline inspection gauge in a pipeline according to claim 1, wherein said means for detecting pressure is a pressure gauge.

5. A system for detecting the location of a pipeline inspection gauge (PIG) in a pipeline, comprising:
   a plurality of hollow, plastic tubes adapted for being positioned at spaced intervals along the length of the pipeline, each of the tubes having an interior, a closed lower end and an open upper end, the closed lower end of each of the tubes being adapted for extending into the pipeline; and
   a plurality of pressure gauges for detecting changes in pressure in the interior of each of the tubes, each of the tubes having a corresponding one of the pressure gauges disposed at the upper end of the tube, each of the tubes being frangible adjacent the lower end so that the PIG breaks the lower end of the tube upon impact, the pressure gauge showing a change in pressure of fluid in the pipeline.

6. The system for detecting the location of a pipeline inspection gauge in a pipeline according to claim 5, wherein each said tube has an exterior surface, the exterior surface being scored adjacent the lower end, said tube being frangible at the score line.

7. A method of detecting the location of a pipeline inspection gauge (PIG) in a pipeline having a product flow therein, comprising the steps of:
   launching the pipeline inspection gauge in the pipeline, the pipeline inspection gauge being propelled by pressure of the product flow;
   positioning tubes along the length of the pipeline, each of the tubes having an upper end, a closed bottom end, and a hollow interior, the closed bottom end extending into the pipeline, each of the tubes being frangible adjacent the bottom end and having a pressure gauge disposed in the upper end, whereby the tube breaks adjacent the bottom end upon impact by the PIG traveling in the pipeline, exposing the interior of the tube to the pressure of the product flow;
   detecting a change in pressure within the interior of the tube caused by the pressure of the product flow, as indicated by the pressure gauge; and
   determining the location of the PIG in the pipeline by a change in the pressure indicated by the pressure gauges as the PIG travels through the pipeline.

* * * * *